United States Patent
Tormo i Blasco et al.

(10) Patent No.: US 7,763,622 B2
(45) Date of Patent: Jul. 27, 2010

(54) SUBSTITUTED 6-(2-HALOGENNPHENYL)-TRIAZOLO-PYRIMIDINES

(75) Inventors: Jordi Tormo i Blasco, Laudenbach (DE); Carsten Blettner, Mannheim (DE); Bernd Müller, Frankenthal (DE); Markus Gewehr, Kastellaun (DE); Wassilios Grammenos, Ludwigshafen (DE); Thomas Grote, Wachenheim (DE); Andreas Gypser, Mannheim (DE); Joachim Rheinheimer, Ludwigshafen (DE); Peter Schäfer, Ottersheim (DE); Frank Schieweck, Heβheim (DE); Anja Schwögler, Mannheim (DE); Eberhard Ammermann, Heppenheim (DE); Siegfried Strathmann, Limburgerhof (DE); Ulrich Schöfl, Brühl (DE); Reinhard Stierl, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 742 days.

(21) Appl. No.: 10/532,719

(22) PCT Filed: Nov. 4, 2003

(86) PCT No.: PCT/EP03/12276

§ 371 (c)(1),
(2), (4) Date: Dec. 20, 2005

(87) PCT Pub. No.: WO2004/041824

PCT Pub. Date: May 21, 2004

(65) Prior Publication Data

US 2006/0241128 A1    Oct. 26, 2006

(30) Foreign Application Priority Data

Nov. 7, 2002 (EP) .................................. 02024808

(51) Int. Cl.
*A01N 43/90* (2006.01)
*A61K 31/519* (2006.01)
*C07D 471/00* (2006.01)
*C07D 487/00* (2006.01)
*C07D 491/00* (2006.01)

(52) U.S. Cl. .................... 514/259.31; 544/255

(58) Field of Classification Search .................. None
See application file for complete search history.

(56) References Cited

U.S. PATENT DOCUMENTS

| | | | |
|---|---|---|---|
| 4,567,263 A | | 1/1986 | Eicken et al. |
| 5,593,996 A | * | 1/1997 | Pees et al. .............. 514/259.31 |
| 5,986,135 A | | 11/1999 | Pfrengle et al. |
| 5,994,360 A | * | 11/1999 | Pfrengle ................. 514/259.31 |
| 6,204,269 B1 | * | 3/2001 | Pfrengle et al. ........ 514/259.31 |
| 6,242,451 B1 | | 6/2001 | Pees |
| 6,737,085 B2 | * | 5/2004 | Nishibe et al. .............. 424/725 |
| 2002/0198222 A1 | | 12/2002 | Bruns et al. |
| 2004/0097522 A1 | | 5/2004 | Gebauer et al. |

FOREIGN PATENT DOCUMENTS

| | | |
|---|---|---|
| EP | 0 071 792 A2 | 2/1983 |
| EP | 0 550 113 A2 | 7/1993 |
| EP | 0834513 B1 | 7/2002 |
| FR | 2 765 875 A1 | 1/1999 |
| FR | 2 784 381 A1 | 4/2000 |
| FR | 2 784 991 A1 | 4/2000 |
| JP | 11035581 * | 2/1999 |
| WO | WO-98/46607 A1 | 10/1998 |
| WO | WO-98/46608 A1 | 10/1998 |
| WO | WO0202563 * | 1/2002 |
| WO | WO-02/50077 A2 | 6/2002 |
| WO | WO-02/094020 A1 | 11/2002 |

OTHER PUBLICATIONS

Meier, et. al., Phosphorous Oxychloride, Encyclopedia of Reagents for Organic Synthesis, 2001, pp. 1-11.*

* cited by examiner

*Primary Examiner*—James O Wilson
*Assistant Examiner*—Jeffrey H Murray
(74) *Attorney, Agent, or Firm*—Birch, Stewart, Kolasch & Birch, LLP

(57) ABSTRACT

Substituted 6-(2-halogenphenyl)-triazolopyrimidines of formula I

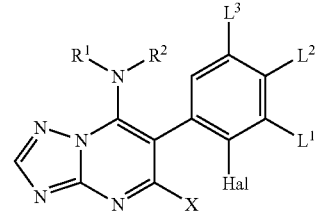

in which $R^1$ denote alkyl, alkenyl, alkynyl, alkadienyl, haloalkyl, haloalkenyl, cycloalkyl, phenyl, naphthyl, or a 5- or 6-membered saturated, unsaturated, or aromatic heterocycle, containing one to four nitrogen atoms or one to three nitrogen atoms and one sulfur or oxygen atom, wherein $R^1$ and $R^2$ radicals may be substituted as defined in the description, $R^2$ denote hydrogen, or a group mentioned for $R^1$; or $R^1$ and $R^2$ together with the interjacent nitrogen atom represent a 5- or 6-membered heterocycle, containing one to four nitrogen atoms or one to three nitrogen atoms and one sulfur or oxygen atom, which ring may be substituted as defined in the description;

Hal is halogen;

$L^1$, $L^3$ independently denote hydrogen, halogen, or alkyl;

$L^2$ is hydrogen, halogen, haloalkyl, or $NH_2$, $NHR^b$, or $N(R^b)_2$, wherein $R^b$ is as defined in the description, wherein at least one from $L^1$, $L^2$, and $L^3$ is not hydrogen;

X is halogen, cyano, alkyl, alkoxy, haloalkoxy or alkenyloxy. processes for their preparation, compositions containing them and to their use for combating phytopathogenic fungi.

9 Claims, No Drawings

SUBSTITUTED 6-(2-HALOGENNPHENYL)-TRIAZOLOPYRIMIDINES

SUMMARY OF THE INVENTION

The invention relates to substituted 6-(2-halogenphenyl)-triazolopyrimidines of formula I

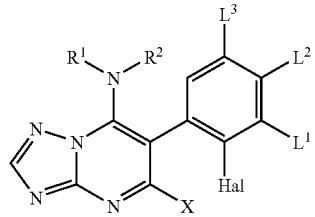

in which

R$^1$ denote C$_1$-C$_{10}$-alkyl, C$_2$-C$_{10}$-alkenyl, C$_2$-C$_{10}$-alkynyl, or C$_4$-C$_{10}$-alkadienyl, C$_1$-C$_{10}$-haloalkyl, C$_2$-C$_{10}$-haloalkenyl, C$_3$-C$_{10}$-cycloalkyl, phenyl, naphthyl, or
a 5- or 6-membered saturated, unsaturated, or aromatic heterocycle, containing one to four nitrogen atoms or one to three nitrogen atoms and one sulfur or oxygen atom,
wherein R$^1$ and R$^2$ radicals may be unsubstituted or partly or fully halogenated or may carry one to three groups R$^a$,
R$^a$ is cyano, nitro, hydroxyl, C$_1$-C$_6$-alkyl, C$_3$-C$_6$-cycloalkyl, C$_1$-C$_6$-alkoxy, C$_1$-C$_6$-alkylthio, C$_1$-C$_6$-alkylamino, di-C$_1$-C$_6$-alkylamino, C$_2$-C$_6$-alkenyl, C$_2$-C$_6$-alkenyloxy, C$_2$-C$_6$-alkynyl, C$_3$-C$_6$-alkynyloxy, or C$_1$-C$_4$-alkylenedioxy;
R$^2$ denote hydrogen, or a group mentioned for R$^1$; or
R$^1$ and R$^2$ together with the interjacent nitrogen atom represent a saturated or partially unsaturated 5- or 6-membered heterocycle, containing one to four nitrogen atoms or one to three nitrogen atoms and one sulfur or oxygen atom, which ring may be substituted by one to three R$^a$ radicals;
Hal is halogen;
L$^1$, L$^3$ independently denote hydrogen, halogen, or C$_1$-C$_4$-alkyl;
L$^2$ is hydrogen, halogen, C$_1$-C$_4$-haloalkyl, or NH$_2$, NHR$^b$, or N(R$^b$)$_2$,
R$^b$ is C$_1$-C$_8$-alkyl, C$_3$-C$_{10}$-alkenyl, C$_3$-C$_{10}$-alkynyl, C$_1$-C$_6$-haloalkyl, C$_3$-C$_6$-haloalkenyl, C$_3$-C$_6$-haloalkynyl, C$_1$-C$_8$-alkoxy-C$_1$-C$_8$-alkyl, C$_1$-C$_8$-alkylthio-C$_1$-C$_8$-alkyl, C$_3$-C$_{10}$-cycloalkyl, or C(=O)-A, in which
A is hydrogen, hydroxy, C$_1$-C$_8$-alkyl, C$_1$-C$_8$-alkoxy, C$_1$-C$_6$-halogenalkoxy, C$_1$-C$_8$-alkylamino or di-(C$_1$-C$_8$-alkyl)amino;
wherein at least one from L$^1$, L$^2$, and L$^3$ is not hydrogen;
X is halogen, cyano, C$_1$-C$_6$-alkyl, C$_1$-C$_6$-alkoxy, C$_1$-C$_6$-haloalkoxy or C$_3$-C$_8$-alkenyloxy.

Moreover, the invention relates to processes for their preparation, compositions containing them and to their use for combating phytopathogenic fungi.

DETAILED DESCRIPTION OF THE INVENTION

6-Phenyl-7-amino-triazolopyrimidines are generally known from U.S. Pat. No. 4,567,262, and EP-A 550 113.
Triazolopyrimidines with a trifluorophenyl group in 6-position are disclosed in WO 98/46607 and EP-A 945 453. From EP-A 834 513 diverse 6-pentafluorophenyl-triazolopyrimidines are known.

The compounds disclosed in the documents discussed above are said to be active against various phytopathogenic fungi.

It is an object of the present invention to provide compounds having improved fungicidal activity.

We have found that this object is achieved by the compounds defined at the outset. Furthermore, we have found processes for their preparation, compositions comprising them and methods for controlling phytopathogenic fungi using the compounds I.

The compounds of formula I differ from the compounds known from closest prior art EP-A 945 453 and EP-A 834 513 in the 6-(2-halogenphenyl) group, which is further substituted in 3-, 4- and/or 5-position.

Compounds of formula I can be prepared similar to the conditions known from EP-A 550 113. Preferably the preparation of compounds of formula I as defined above comprises reacting 5-amino-triazole with 2-(2-halogenphenyl)-substituted malonic acid ester of formula II, in which

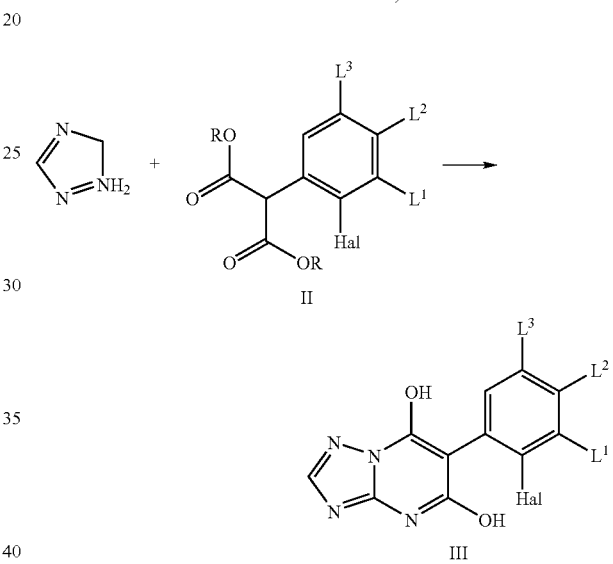

R represents alkyl, preferably C$_1$-C$_6$-alkyl, in particular methyl or ethyl, under alkaline conditions, preferably using high boiling tertiary amines as for example tri-n-butylamine as disclosed for example by EP-A 770 615 to yield compounds of formula III.

The resulting 5,7-dihydroxy-6-phenyl-triazolopyrimidine of formula III, wherein L$^1$ to L$^3$ are as defined for formula I, is subsequently treated with a halogenating agent, preferably with a brominating or chlorinating agent, such as phosphorus oxybromide or phosphorus oxychloride, neat or in the presence of a solvent to give IV, wherein Y is halogen, such as chlorine or bromine.

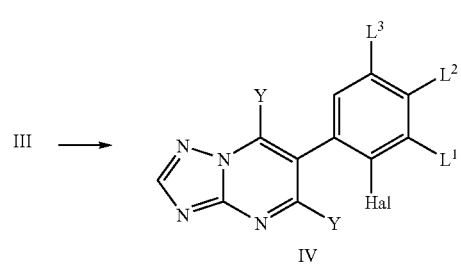

The reaction is suitably carried out at a temperature in the range from 0° C. to 150° C., the preferred reaction temperature being from 80° C. to 125° C. as disclosed for example by EP-A 770 615.

Dihalotriazolopyrimidine IV is further reacted with an amine of formula V

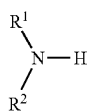

V in which $R^1$ and $R^2$ are as defined in formula I to produce compounds of formula I in which X is halogen.

The reaction between the 5,7-dihalo compound IV and the amine of formula V can be carried out under conditions known from WO 98/46608. The reaction is preferably carried out in the presence of a solvent. Suitable solvents include ethers, such as dioxane, diethyl ether and, especially, tetrahydrofuran, halogenated hydrocarbons such as dichloromethane and aromatic hydrocarbons, for example toluene.

The reaction is suitably carried out at a temperature in the range from 0° C. to 70° C., the preferred reaction temperature being from 10° C. to 35° C.

It is also preferred that the reaction is carried out in the presence of a base. Suitable bases include tertiary amines, such as triethylamine, and inorganic bases, such as potassium carbonate or sodium carbonate. Alternatively, an excess of the compound of formula V may serve as a base.

Compounds of formula I in which X denotes cyano, $C_1$-$C_6$-alkoxy, $C_1$-$C_6$-haloalkoxy or $C_3$-$C_8$-alkenyloxy can be prepared by reacting compounds I' in which Y is halogen, preferably chloro, with compounds of formula VI, which are, dependent from the value of X' to be introduced to yield formula I compounds, an anorganic cyano salt, an alkoxylate, haloalkoxylate or an alkenyloxylate, respectively, preferably in the presence of a solvent. The cation M in formula VI has minor influence; for practical and economical reasons usually ammonium-, tetraalkylammonium- or alkalimetal- and earth metal salts are preferred.

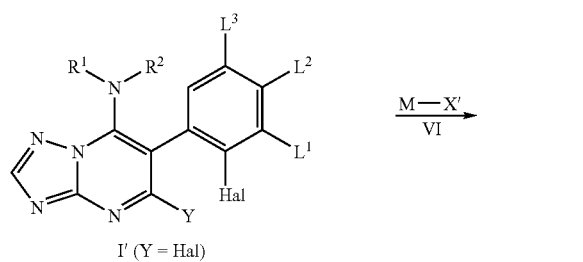

I' (Y = Hal)

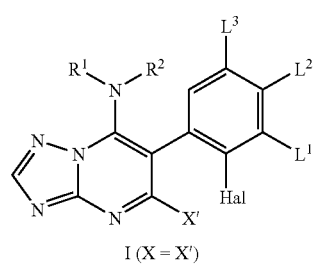

I (X = X')

The reaction is suitably carried out at a temperature in the range from 0 to 120° C., the preferred reaction temperature being from 10 to 40° C. [cf. J. Heterocycl. Chem. Vol. 12, p. 861-863 (1975)].

Suitable solvents include ethers, such as dioxane, diethyl ether and, especially, tetrahydrofuran, halogenated hydrocarbons such as dichloromethane and aromatic hydrocarbons, for example toluene.

Compounds of formula I in which X denotes $C_1$-$C_6$-alkyl can be prepared by reacting compounds I in which X is halogen, preferably chloro, with malonic acid esters of formula VII, wherein X" denotes H or $C_1$-$C_5$-alkyl and R denotes $C_1$-$C_4$-alkyl, to compounds of formula VIII and decarboxylation under conditions described in U.S. Pat. No. 5,994,360.

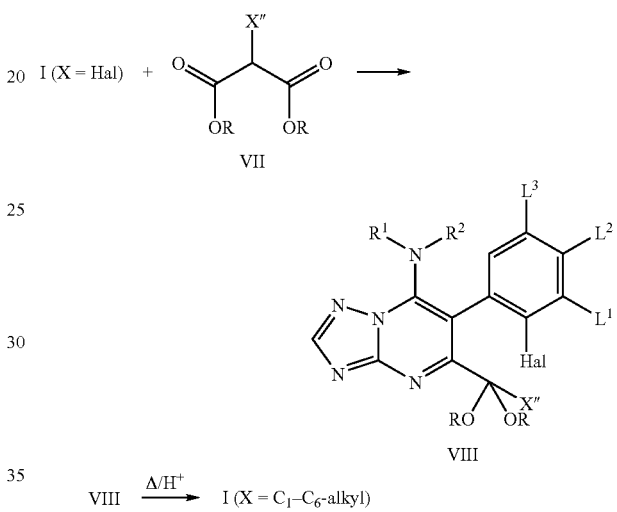

Accordingly, the invention relates to the novel intermediates of formulae II, III and IV.

The compounds of formula II are preferably prepared by reaction of the corresponding substituted bromobenzenes with sodium dialkylmalonates in the presence of a copper(I) salt [cf. Chemistry Letters, pp. 367-370, 1981; EP-A 10 02 788].

The compounds of formula II may also be prepared by reaction of an alkyl 2-(2-halogenphenyl)-acetate with dialkylcarbonate in the presence of a strong base, preferably sodium ethoxide and sodium hydride (cf. Heterocycles, pp. 1031-1047, 1996).

The substituted phenylacetates which are the starting compounds for compounds of formula II are known and commercially available, and/or they are obtainable by generally known methods.

The reaction mixtures are worked up in a customary manner, for example by mixing with water, phase separation and, if required, chromatographic purification of the crude products. Some of the end products are obtained in the form of colorless or slightly brownish, viscous oils, which are purified or freed from volatile components under reduced pressure and at moderately elevated temperatures. If the end products are obtained as solids, purification can also be carried out by recrystallization or digestion.

If individual compounds I are not obtainable by the routes described above, they can be prepared by derivatization of other compounds I.

In the symbol definitions given in the formulae above, collective terms were used which generally represent the following substituents:

Halogen: fluorine, chlorine, bromine and iodine;

$C_1$-$C_{10}$-alkyl: saturated, straight-chain or branched hydrocarbon radicals having 1 to 10, especially 1 to 6 carbon atoms, for example $C_1$-$C_4$-alkyl as mentioned above or pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_2$-$C_{10}$-alkenyl: unsaturated, straight-chain or branched hydrocarbon radicals having 2 to 10, especially 2 to 6 carbon atoms and a double bond in any position, for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl;

$C_2$-$C_{10}$-alkynyl: straight-chain or branched hydrocarbon radicals having 2 to 10, especially 2 to 4 carbon atoms and a triple bond in any position, for example ethynyl, 1-propynyl, 2-propynyl, 1-butynyl, 2-butynyl, 3-butynyl and 1-methyl-2-propynyl;

$C_3$-$C_{10}$-cycloalkyl: mono- or bicyclic cycloalkyl groups having 3 to 10 carbon atoms; monocyclic groups preferably have 3 to 8, especially 3 to 6 ring members, bicyclic groups preferably have 8 to 10 ring members.

A 5- or 6-membered saturated or partially unsaturated heterocycle, containing one to four nitrogen atoms or one to three nitrogen atoms and one sulfur or oxygen atom, preferably one oxygen atom, for example saturated heterocycles such as 1-pyrimidinyl, 2-pyrimidinyl, morpholin-4-yl, thiomorpholin-4-yl; or partially unsaturated heterocycles, containing one C=C or one N=C double bond, such as 3,6-dihydro-2H-pyridin-1-yl, or 2,5-dihydropyrrol-1-yl;

A 5-membered aromatic heterocycle, containing one to four nitrogen atoms or one to three nitrogen atoms and one sulfur or oxygen atom: 5-membered heteroaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered aromatic heterocycle, containing one to four nitrogen atoms: 6-membered heteroaryl groups which, in addition to carbon atoms, may contain one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl, preferably pyridyl, pyrimidyl, pyrazolyl or thienyl.

With respect to their intended use, preference is given to triazolopyrimidines of the formula I having the following substituents, where the preference is valid in each case on its own or in combination:

A preferred cycloalkyl moiety is cyclopentyl being optionally substituted by one or more nitro, cyano, $C_1$-$C_6$-alkyl, $C_1$-$C_6$-alkoxy groups.

Preference is given to compounds of formula I in which any alkyl or haloalkyl part of the groups $R^1$ or $R^2$, which may be straight chained or branched, contains up to 10 carbon atoms, preferably 1 to 9 carbon atoms, more preferably 2 to 6 carbon atoms, any alkenyl or alkynyl part of the substituents $R^1$ or $R^2$ contains up to 10 carbon atoms, preferably 2 to 9 carbon atoms, more preferably 3 to 6 carbon atoms, any cycloalkyl part of the substituents $R^1$ or $R^2$ contains from 3 to 10 carbon atoms, preferably from 3 to 8 carbon atoms, more preferably from 3 to 6 carbon atoms, and any bicycloalkyl part of the substituents $R^1$ or $R^2$ contains from 5 to 9 carbon atoms, preferably from 7 to 9 carbon atoms. Any alkyl, alkenyl or alkynyl group may be linear or branched.

Compounds of formula I are preferred in which $R^1$ represents a straight-chained or branched $C_1$-$C_{10}$-alkyl, in particular a branched $C_3$-$C_{10}$-alkyl group, a $C_3$-$C_8$-cycloalkyl, a $C_5$-$C_9$-bicycloalkyl, a $C_3$-$C_8$-cycloalkyl-$C_1$-$C_6$-alkyl, $C_1$-$C_{10}$-alkoxy-$C_1$-$C_6$-alkyl, a $C_1$-$C_{10}$-haloalkyl or a phenyl group being optionally substituted by one to three halogen atoms or $C_1$-$C_{10}$-alkyl or $C_1$-$C_{10}$-alkoxy groups.

Moreover, particular preference is given to compounds I in which $R^1$ and $R^2$ together with the interjacent nitrogen atom form an optionally substituted heterocyclic ring, preferably an optionally substituted $C_3$-$C_7$-heterocyclic ring, in particular a 5- or 6-membered saturated heterocycle, such as pyrrolidine, piperidine, morpholine, or tetrahydropyridine, or a 5- or 6-membered partially unsaturated heterocycle, such as 3,6-dihydro-2H-pyridin-1-yl, or 2,5-dihydropyrrol-1-yl, wherein the saturated or unsaturated heterocycle is optionally substituted by one or more $C_1$-$C_4$-alkyl or $C_1$-$C_2$-haloalkyl groups, preferably by one or two methyl groups. Particular preference is given to compounds I, in which $R^1$ and $R^2$ together form a 4-methylpiperidin-1-yl group.

Furthermore, particular preference is given to compounds I in which $R^2$ represents hydrogen, $C_1$-$C_{10}$-alkyl or $C_1$-$C_{10}$-haloalkyl, in particular hydrogen.

Moreover, particular preference is given to compounds I in which $R^2$ is methyl or ethyl.

If $R^1$ denotes $C_1$-$C_{10}$-haloalkyl, preferably polyfluorinated alkyl, in particular 2,2,2-trifluoroethyl, 2-(1,1,1-trifluoropropyl) or 2-(1,1,1-trifluorobutyl), $R^2$ preferably represents hydrogen.

Particular preference is given to compounds I in which Hal is fluoro, chloro, or bromo, particularly fluoro.

Furthermore, preference is given to compounds I in which $L^1$ is hydrogen, or fluoro, particularly hydrogen.

Besides, particular preference is given to compounds I in which $L^2$ is hydrogen, fluoro, trifluoromethyl, amino, dimethylamino, or N-acetylamino, particularly fluoro.

Futhermore, preference is given to compounds I in which $L^2$ is $NHR^b$ or $N(R^b)_2$, wherein $R^b$ is methyl or $C(=O)$—$C_1$-$C_4$-alkyl.

Likewise, particular preference is given to compounds I in which $L^3$ is hydrogen, fluoro, methyl, particularly hydrogen.

A particularly preferred embodiment of the present invention are compounds of formula I, in which the 6-(2-halophenyl) group represents one of the following moieties:

2,3,5-trifluorophenyl, 2,4-difluorophenyl, 2-F,4-$CF_3$-phenyl, 2-F,5-$CH_3$-phenyl, 2-Cl,4-F-phenyl, 2-F,4-Cl-phenyl, 2-F,4-Br-pheyl, 2-Cl,4-Br-phenyl, 2,3-difluorophenyl, 2,4-difluorophenyl, 2,4,5-trifluorophenyl, 2,3,4-trifluorophenyl, 2-F,4-$NH_2$-phenyl, 2-F,4-$N(CH_3)_2$-phenyl, 2-F,4-NHC(O)$CH_3$-phenyl, 2-Br,3,5-difluorophenyl, 2-F,4-$NO_2$-phenyl, and 2-Cl,4-$NO_2$-phenyl.

Moreover, preference is given to compounds I in which X is halogen, cyano or methyl, preferably halogen, such as chloro or bromo, particularly chloro.

The particularly preferred embodiments of the intermediates with respect to the variables correspond to those of the radicals X and $L^1$ to $L^3$ of formula I.

Included in the scope of the present invention are (R) and (S) isomers of compounds of general formula I having a chiral center and the racemates thereof, and salts, N-oxides and acid addition compounds.

With respect to their use, particular preference is given to the compounds I compiled in the tables below. The groups mentioned in the tables for a substituent are furthermore for their part, independently of the combination in which they are mentioned, a particularly preferred embodiment of the respective substituents.

Table 1
Compounds of formula I, in which X is chloro, Hal, $L^1$ and $L^3$ are fluoro, $L^2$ is hydrogen and $R^1$ and $R^2$ correspond to one row in Table A Table 2
Compounds of formula I, in which X is cyano, Hal, $L^1$ and $L^3$ are fluoro, $L^2$ is hydrogen and $R^1$ and $R^2$ correspond to one row in Table A Table 3
Compounds of formula I, in which X is methyl, Hal, $L^1$ and $L^3$ are fluoro, $L^2$ is hydrogen and $R^1$ and $R^2$ correspond to one row in Table A Table 4
Compounds of formula I, in which X is methoxy, Hal, $L^1$ and $L^3$ are fluoro, $L^2$ is hydrogen and $R^1$ and $R^2$ correspond to one row in Table A Table 5
Compounds of formula I, in which X is chloro, Hal and $L^2$ are fluoro, $L^1$ and $L^3$ are hydrogen and $R^1$ and $R^2$ correspond to one row in Table A Table 6
Compounds of formula I, in which X is cyano, Hal and $L^2$ are fluoro, $L^1$ and $L^3$ are hydrogen and $R^1$ and $R^2$ correspond to one row in Table A Table 7
Compounds of formula I, in which X is methyl, Hal and $L^2$ are fluoro, $L^1$ and $L^3$ are hydrogen and $R^1$ and $R^2$ correspond to one row in Table A Table 8
Compounds of formula I, in which X is methoxy, Hal and $L^2$ are fluoro, $L^1$ and $L^3$ are hydrogen and $R^1$ and $R^2$ correspond to one row in Table A Table 9
Compounds of formula I, in which X is chloro, Hal is fluoro, $L^1$ and $L^3$ are hydrogen, $L^2$ is trifluoromethyl and $R^1$ and $R^2$ correspond to one row in Table A Table 10
Compounds of formula I, in which X is cyano, Hal is fluoro, $L^1$ and $L^3$ are hydrogen, $L^2$ is trifluoromethyl and $R^1$ and $R^2$ correspond to one row in Table A Table 11
Compounds of formula I, in which X is methyl, Hal is fluoro, $L^1$ and $L^3$ are hydrogen, $L^2$ is trifluoromethyl and $R^1$ and $R^2$ correspond to one row in Table A Table 12
Compounds of formula I, in which X is methoxy, Hal is fluoro, $L^1$ and $L^3$ are hydrogen, $L^2$ is trifluoromethyl and $R^1$ and $R^2$ correspond to one row in Table A Table 13
Compounds of formula I, in which X is chloro, Hal is fluoro, $L^1$ and $L^2$ are hydrogen, $L^3$ is methyl and $R^1$ and $R^2$ correspond to one row in Table A Table 14
Compounds of formula I, in which X is cyano, Hal is fluoro, $L^1$ and $L^2$ are hydrogen, $L^3$ is methyl and $R^1$ and $R^2$ correspond to one row in Table A Table 15
Compounds of formula I, in which X is methyl, Hal is fluoro, $L^1$ and $L^2$ are hydrogen, $L^3$ is methyl and $R^1$ and $R^2$ correspond to one row in Table A Table 16
Compounds of formula I, in which X is methoxy, Hal is fluoro, $L^1$ and $L^2$ are hydrogen, $L^3$ is methyl and $R^1$ and $R^2$ correspond to one row in Table A Table 17
Compounds of formula I, in which X and Hal are chloro, $L^1$ and $L^3$ are hydrogen, $L^2$ is fluoro and $R^1$ and $R^2$ correspond to one row in Table A Table 18
Compounds of formula I, in which X is cyano, Hal is chloro, $L^1$ and $L^3$ are hydrogen, $L^2$ is fluoro and $R^1$ and $R^2$ correspond to one row in Table A Table 19
Compounds of formula I, in which X is methyl, Hal is chloro, $L^1$ and $L^3$ are hydrogen, $L^2$ is fluoro and $R^1$ and $R^2$ correspond to one row in Table A Table 20
Compounds of formula I, in which X is methoxy, Hal is chloro, $L^1$ and $L^3$ are hydrogen, $L^2$ is fluoro and $R^1$ and $R^2$ correspond to one row in Table A Table 21
Compounds of formula I, in which X is chloro, Hal is fluoro, $L^1$ and $L^3$ are hydrogen, $L^2$ is chloro and $R^1$ and $R^2$ correspond to one row in Table A Table 22
Compounds of formula I, in which X is cyano, Hal is fluoro, $L^1$ and $L^3$ are hydrogen, $L^2$ is chloro and $R^1$ and $R^2$ correspond to one row in Table A Table 23
Compounds of formula I, in which X is methyl, Hal is fluoro, $L^1$ and $L^3$ are hydrogen, $L^2$ is chloro and $R^1$ and $R^2$ correspond to one row in Table A Table 24
Compounds of formula I, in which X is methoxy, Hal is fluoro, $L^1$ and $L^3$ are hydrogen, $L^2$ is chloro and $R^1$ and $R^2$ correspond to one row in Table A Table 25
Compounds of formula I, in which X is chloro, Hal is fluoro, $L^1$ and $L^3$ are hydrogen, $L^2$ is bromo and $R^1$ and $R^2$ correspond to one row in Table A Table 26
Compounds of formula I, in which X is cyano, Hal is fluoro, $L^1$ and $L^3$ are hydrogen, $L^2$ is bromo and $R^1$ and $R^2$ correspond to one row in Table A Table 27
Compounds of formula I, in which X is methyl, Hal is fluoro, $L^1$ and $L^3$ are hydrogen, $L^2$ is bromo and $R^1$ and $R^2$ correspond to one row in Table A Table 28
Compounds of formula I, in which X is methoxy, Hal is fluoro, $L^1$ and $L^3$ are hydrogen, $L^2$ is bromo and $R^1$ and $R^2$ correspond to one row in Table A Table 29
Compounds of formula I, in which X and Hal are chloro, $L^1$ and $L^3$ are hydrogen, $L^2$ is bromo and $R^1$ and $R^2$ correspond to one row in Table A Table 30
Compounds of formula I, in which X is cyano, Hal is chloro, $L^1$ and $L^3$ are hydrogen, $L^2$ is bromo and $R^1$ and $R^2$ correspond to one row in Table A Table 31
Compounds of formula I, in which X is methyl, Hal is chloro, $L^1$ and $L^3$ are hydrogen, $L^2$ is bromo and $R^1$ and $R^2$ correspond to one row in Table A Table 32
Compounds of formula I, in which X is methoxy, Hal is chloro, $L^1$ and $L^3$ are hydrogen, $L^2$ is bromo and $R^1$ and $R^2$ correspond to one row in Table A Table 33
Compounds of formula I, in which X, Hal and $L^2$ are chloro, $L^1$ and $L^3$ are hydrogen and $R^1$ and $R^2$ correspond to one row in Table A Table 34
Compounds of formula I, in which X is cyano, Hal and $L^2$ are chloro, $L^1$ and $L^3$ are hydrogen and $R^1$ and $R^2$ correspond to one row in Table A Table 35
Compounds of formula I, in which X is methyl, Hal and $L^2$ are chloro, $L^1$ and $L^3$ are hydrogen and $R^1$ and $R^2$ correspond to one row in Table A Table 36
Compounds of formula I, in which X is methoxy, Hal and $L^2$ are chloro, $L^1$ and $L^3$ are hydrogen and $R^1$ and $R^2$ correspond to one row in Table A Table 37
Compounds of formula I, in which X is chloro, Hal and $L^1$ are fluoro, $L^2$ and $L^3$ are hydrogen and $R^1$ and $R^2$ correspond to one row in Table A Table 38
Compounds of formula I, in which X is cyano, Hal and $L^1$ are fluoro, $L^2$ and $L^3$ are hydrogen and $R^1$ and $R^2$ correspond to one row in Table A Table 39
Compounds of formula I, in which X is methyl, Hal and $L^1$ are fluoro, $L^2$ and $L^3$ are hydrogen and $R^1$ and $R^2$ correspond to one row in Table A Table 40
Compounds of formula I, in which X is methoxy, Hal and $L^1$ are fluoro, $L^2$ and $L^3$ are hydrogen and $R^1$ and $R^2$ correspond to one row in Table A Table 41
Compounds of formula I, in which X is chloro, Hal and $L^3$ are fluoro, $L^1$ and $L^2$ hydrogen and $R^1$ and $R^2$ correspond to one row in Table A Table 42
Compounds of formula I, in which X is cyano, Hal and $L^3$ are fluoro, $L^1$ and $L^2$ hydrogen and $R^1$ and $R^2$ correspond to one row in Table A Table 43
Compounds of formula I, in which X is methyl, Hal and $L^3$ are fluoro, $L^1$ and $L^2$ hydrogen and $R^1$ and $R^2$ correspond to one row in Table A Table 44
Compounds of formula I, in which X is methoxy, Hal and $L^3$ are fluoro, $L^1$ and $L^2$ hydrogen and $R^1$ and $R^2$ correspond to one row in Table A Table 45
Compounds of formula I, in which X is chloro, Hal, $L^2$ and $L^3$ are fluoro, $L^1$ is hydrogen and $R^1$ and $R^2$ correspond to one row in Table A Table 46
Compounds of formula I, in which X is cyano, Hal, $L^2$ and $L^3$ are fluoro, $L^1$ is hydrogen and $R^1$ and $R^2$ correspond to one row in Table A Table 47
Compounds of formula I, in which X is methyl, Hal, $L^2$ and $L^3$ are fluoro, $L^1$ is hydrogen and $R^1$ and $R^2$ correspond to one row in Table A Table 48
Compounds of formula I, in which X is methoxy, Hal, $L^2$ and $L^3$ are fluoro, $L^1$ is hydrogen and $R^1$ and $R^2$ correspond to one row in Table A Table 49
Compounds of formula I, in which X is chloro, Hal, $L^1$ and $L^2$ are fluoro, $L^3$ is hydrogen and $R^1$ and $R^2$ correspond to one row in Table A Table 50
Compounds of formula I, in which X is cyano, Hal, $L^1$ and $L^2$ are fluoro, $L^3$ is hydrogen and $R^1$ and $R^2$ correspond to one row in Table A Table 51
Compounds of formula I, in which X is methyl, Hal, $L^1$ and $L^2$ are fluoro, $L^3$ is hydrogen and $R^1$ and $R^2$ correspond to one row in Table A Table 52
Compounds of formula I, in which X is methoxy, Hal, $L^1$ and $L^2$ are fluoro, $L^3$ is hydrogen and $R^1$ and $R^2$ correspond to one row in Table A Table 53
Compounds of formula I, in which X is chloro, Hal is bromo, $L^1$ and $L^3$ are fluoro, $L^2$ is hydrogen and $R^1$ and $R^2$ correspond to one row in Table A Table 54
Compounds of formula I, in which X is cyano, Hal is bromo, $L^1$ and $L^3$ are fluoro, $L^2$ is hydrogen and $R^1$ and $R^2$ correspond to one row in Table A Table 55
Compounds of formula I, in which X is methyl, Hal is bromo, $L^1$ and $L^3$ are fluoro, $L^2$ is hydrogen and $R^1$ and $R^2$ correspond to one row in Table A Table 56
Compounds of formula I, in which X is methoxy, Hal is bromo, $L^1$ and $L^3$ are fluoro, $L^2$ is hydrogen and $R^1$ and $R^2$ correspond to one row in Table A Table 57
Compounds of formula I, in which X is chloro, Hal is fluoro, $L^1$ and $L^3$ are hydrogen, $L^2$ is amino and $R^1$ and $R^2$ correspond to one row in Table A Table 58
Compounds of formula I, in which X is cyano, Hal is fluoro, $L^1$ and $L^3$ are hydrogen, $L^2$ is amino and $R^1$ and $R^2$ correspond to one row in Table A Table 59
Compounds of formula I, in which X is methyl, Hal is fluoro, $L^1$ and $L^3$ are hydrogen, $L^2$ is amino and $R^1$ and $R^2$ correspond to one row in Table A Table 60
Compounds of formula I, in which X is methoxy, Hal is fluoro, $L^1$ and $L^3$ are hydrogen, $L^2$ is amino and $R^1$ and $R^2$ correspond to one row in Table A Table 61
Compounds of formula I, in which X is chloro, Hal is fluoro, $L^1$ and $L^3$ are hydrogen, $L^2$ is methylamino and $R^1$ and $R^2$ correspond to one row in Table A Table 62
Compounds of formula I, in which X is cyano, Hal is fluoro, $L^1$ and $L^3$ are hydrogen, $L^2$ is methylamino and $R^1$ and $R^2$ correspond to one row in Table A Table 63
Compounds of formula I, in which X is methyl, Hal is fluoro, $L^1$ and $L^3$ are hydrogen, $L^2$ is methylamino and $R^1$ and $R^2$ correspond to one row in Table A Table 64
Compounds of formula I, in which X is methoxy, Hal is fluoro, $L^1$ and $L^3$ are hydrogen, $L^2$ is methylamino and $R^1$ and $R^2$ correspond to one row in Table A Table 65
Compounds of formula I, in which X is chloro, Hal is fluoro, $L^1$ and $L^3$ are hydrogen, $L^2$ is dimethylamino and $R^1$ and $R^2$ correspond to one row in Table A Table 66
Compounds of formula I, in which X is cyano, Hal is fluoro, $L^1$ and $L^3$ are hydrogen, $L^2$ is dimethylamino and $R^1$ and $R^2$ correspond to one row in Table A Table 67
Compounds of formula I, in which X is methyl, Hal is fluoro, $L^1$ and $L^3$ are hydrogen, $L^2$ is dimethylamino and $R^1$ and $R^2$ correspond to one row in Table A Table 68
Compounds of formula I, in which X is methoxy, Hal is fluoro, $L^1$ and $L^3$ are hydrogen, $L^2$ is dimethylamino and $R^1$ and $R^2$ correspond to one row in Table A Table 69
Compounds of formula I, in which X is chloro, Hal is fluoro, $L^1$ and $L^3$ are hydrogen, $L^2$ is N-acetylamino and $R^1$ and $R^2$ correspond to one row in Table A Table 70
Compounds of formula I, in which X is cyano, Hal is fluoro, $L^1$ and $L^3$ are hydrogen, $L^2$ is N-acetylamino and $R^1$ and $R^2$ correspond to one row in Table A Table 71
Compounds of formula I, in which X is methyl, Hal is fluoro, $L^1$ and $L^3$ are hydrogen, $L^2$ is N-acetylamino and $R^1$ and $R^2$ correspond to one row in Table A Table 72
Compounds of formula I, in which X is methoxy, Hal is fluoro, $L^1$ and $L^3$ are hydrogen, $L^2$ is N-acetylamino and $R^1$ and $R^2$ correspond to one row in Table A

TABLE A

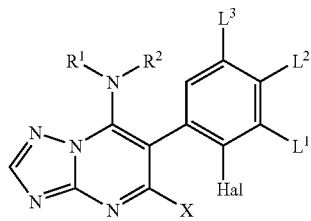

| No. | $R^1$ | $R^2$ |
|---|---|---|
| A-1 | $CH_2CH_3$ | H |
| A-2 | $CH_2CH_3$ | $CH_3$ |
| A-3 | $CH_2CH_3$ | $CH_2CH_3$ |
| A-4 | $CH_2CF_3$ | H |
| A-5 | $CH_2CF_3$ | $CH_3$ |
| A-6 | $CH_2CF_3$ | $CH_2CH_3$ |
| A-7 | $CH_2CCl_3$ | H |
| A-8 | $CH_2CCl_3$ | $CH_3$ |
| A-9 | $CH_2CCl_3$ | $CH_2CH_3$ |
| A-10 | $CH_2CH_2CH_3$ | H |
| A-11 | $CH_2CH_2CH_3$ | $CH_3$ |
| A-12 | $CH_2CH_2CH_3$ | $CH_2CH_3$ |
| A-13 | $CH_2CH_2CH_3$ | $CH_2CH_2CH_3$ |
| A-14 | $CH(CH_3)_2$ | H |
| A-15 | $CH(CH_3)_2$ | $CH_3$ |
| A-16 | $CH(CH_3)_2$ | $CH_2CH_3$ |
| A-17 | (±) $CH(CH_3)-CH_2CH_3$ | H |
| A-18 | (±) $CH(CH_3)-CH_2CH_3$ | $CH_3$ |
| A-19 | (±) $CH(CH_3)-CH_2CH_3$ | $CH_2CH_3$ |
| A-20 | (S) $CH(CH_3)-CH_2CH_3$ | H |
| A-21 | (S) $CH(CH_3)-CH_2CH_3$ | $CH_3$ |
| A-22 | (S) $CH(CH_3)-CH_2CH_3$ | $CH_2CH_3$ |
| A-23 | (R) $CH(CH_3)-CH_2CH_3$ | H |
| A-24 | (R) $CH(CH_3)-CH_2CH_3$ | $CH_3$ |
| A-25 | (R) $CH(CH_3)-CH_2CH_3$ | $CH_2CH_3$ |
| A-26 | (±) $CH(CH_3)-CH(CH_3)_2$ | H |
| A-27 | (±) $CH(CH_3)-CH(CH_3)_2$ | $CH_3$ |
| A-28 | (±) $CH(CH_3)-CH(CH_3)_2$ | $CH_2CH_3$ |
| A-29 | (S) $CH(CH_3)-CH(CH_3)_2$ | H |
| A-30 | (S) $CH(CH_3)-CH(CH_3)_2$ | $CH_3$ |
| A-31 | (S) $CH(CH_3)-CH(CH_3)_2$ | $CH_2CH_3$ |
| A-32 | (R) $CH(CH_3)-CH(CH_3)_2$ | H |
| A-33 | (R) $CH(CH_3)-CH(CH_3)_2$ | $CH_3$ |
| A-34 | (R) $CH(CH_3)-CH(CH_3)_2$ | $CH_2CH_3$ |
| A-35 | (±) $CH(CH_3)-C(CH_3)_3$ | H |
| A-36 | (±) $CH(CH_3)-C(CH_3)_3$ | $CH_3$ |
| A-37 | (±) $CH(CH_3)-C(CH_3)_3$ | $CH_2CH_3$ |
| A-38 | (S) $CH(CH_3)-C(CH_3)_3$ | H |
| A-39 | (S) $CH(CH_3)-C(CH_3)_3$ | $CH_3$ |
| A-40 | (S) $CH(CH_3)-C(CH_3)_3$ | $CH_2CH_3$ |
| A-41 | (R) $CH(CH_3)-C(CH_3)_3$ | H |
| A-42 | (R) $CH(CH_3)-C(CH_3)_3$ | $CH_3$ |
| A-43 | (R) $CH(CH_3)-C(CH_3)_3$ | $CH_2CH_3$ |
| A-44 | (±) $CH(CH_3)-CF_3$ | H |
| A-45 | (±) $CH(CH_3)-CF_3$ | $CH_3$ |
| A-46 | (±) $CH(CH_3)-CF_3$ | $CH_2CH_3$ |
| A-47 | (S) $CH(CH_3)-CF_3$ | H |
| A-48 | (S) $CH(CH_3)-CF_3$ | $CH_3$ |
| A-49 | (S) $CH(CH_3)-CF_3$ | $CH_2CH_3$ |
| A-50 | (R) $CH(CH_3)-CF_3$ | H |
| A-51 | (R) $CH(CH_3)-CF_3$ | $CH_3$ |
| A-52 | (R) $CH(CH_3)-CF_3$ | $CH_2CH_3$ |
| A-53 | (±) $CH(CH_3)-CCl_3$ | H |
| A-54 | (±) $CH(CH_3)-CCl_3$ | $CH_3$ |
| A-55 | (±) $CH(CH_3)-CCl_3$ | $CH_2CH_3$ |
| A-56 | (S) $CH(CH_3)-CCl_3$ | H |
| A-57 | (S) $CH(CH_3)-CCl_3$ | $CH_3$ |
| A-58 | (S) $CH(CH_3)-CCl_3$ | $CH_2CH_3$ |
| A-59 | (R) $CH(CH_3)-CCl_3$ | H |
| A-60 | (R) $CH(CH_3)-CCl_3$ | $CH_3$ |
| A-61 | (R) $CH(CH_3)-CCl_3$ | $CH_2CH_3$ |
| A-62 | $CH_2CF_2CF_3$ | H |
| A-63 | $CH_2CF_2CF_3$ | $CH_3$ |
| A-64 | $CH_2CF_2CF_3$ | $CH_2CH_3$ |

TABLE A-continued

[Structure I: A triazolopyrimidine with R¹R²N- group, and phenyl substituted with L¹, L², L³, Hal, and X]

| No. | R¹ | R² |
|---|---|---|
| A-65 | CH$_2$(CF$_2$)$_2$CF$_3$ | H |
| A-66 | CH$_2$(CF$_2$)$_2$CF$_3$ | CH$_3$ |
| A-67 | CH$_2$(CF$_2$)$_2$CF$_3$ | CH$_2$CH$_3$ |
| A-68 | CH$_2$C(CH$_3$)=CH$_2$ | H |
| A-69 | CH$_2$C(CH$_3$)=CH$_2$ | CH$_3$ |
| A-70 | CH$_2$C(CH$_3$)=CH$_2$ | CH$_2$CH$_3$ |
| A-71 | cyclopentyl | H |
| A-72 | cyclopentyl | CH$_3$ |
| A-73 | cyclopentyl | CH$_2$CH$_3$ |
| A-74 | Cyclohexyl | H |
| A-75 | Cyclohexyl | CH$_3$ |
| A-76 | Cyclohexyl | CH$_2$CH$_3$ |
| A-77 | —(CH$_2$)$_2$CH=CHCH$_2$— | |
| A-78 | —(CH$_2$)$_2$C(CH$_3$)=CHCH$_2$— | |
| A-79 | —(CH$_2$)$_2$CH(CH$_3$)(CH$_2$)$_2$— | |
| A-80 | —(CH$_2$)$_2$CHF(CH$_2$)$_2$— | |
| A-81 | —(CH$_2$)$_3$CHFCH$_2$— | |
| A-82 | —(CH$_2$)$_2$CH(CF$_3$)(CH$_2$)$_2$— | |
| A-83 | —(CH$_2$)$_2$O(CH$_2$)$_2$— | |
| A-84 | —(CH$_2$)$_2$S(CH$_2$)$_2$— | |
| A-85 | —(CH$_2$)$_5$— | |
| A-86 | —(CH$_2$)$_4$— | |
| A-87 | —CH$_2$CH=CHCH$_2$— | |
| A-88 | —CH(CH$_3$)(CH$_2$)$_3$— | |
| A-89 | —CH$_2$CH(CH$_3$)(CH$_2$)$_2$— | |

The compounds I are suitable as fungicides. They are distinguished by an outstanding activity against a broad spectrum of phytopathogenic fungi, in particular from the classes of the Ascomycetes, Deuteromycetes, Oomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

*Alternaria* species on vegetables and fruit,
*Bipolaris* and *Drechslera* species on cereals, rice and turf,
*Blumeria graminis* (powdery mildew) on cereals,
*Botrytis cinerea* (gray mold) on strawberries, vegetables, or namentals and grapevines,
*Erysiphe cichoracearum* and *Sphaerotheca fuliginea* on cucurbits,
*Fusarium* and *Verticillium* species on various plants,
*Mycosphaerella* species on cereals, bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Rhizoctonia* species on cotton, rice and turf,
*Septoria tritici* and *Stagonospora nodorum* on wheat,
*Uncinula necator* on grapevines,
*Ustilago* species on cereals and sugar cane, and
*Venturia* species (scab) on apples and pears.

Moreover, the compounds I are suitable for controlling harmful fungi such as *Paecilomyces variotii* in the protection of materials (e.g. wood, paper, paint dispersions, fibers and fabrics) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise between 0.1 and 95, preferably 0.5 and 90% by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

The compounds I can be converted into the customary formulations, eg. solutions, emulsions, suspensions, dusts, powders, pastes and granules. The use form depends on the particular purpose; it is intended to ensure in each case a fine and uniform distribution of the compound according to the invention.

The formulations are prepared in a known manner, eg. by extending the active ingredient with solvents and/or carriers, if desired using emulsifiers and dispersants. Solvents/auxiliaries which are suitable are essentially:

water, aromatic solvents (for example SOLVESSO products, xylene), paraffins (for example mineral fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used;

carriers such as ground natural minerals (eg, kaolins, clays, talc, chalk) and ground synthetic minerals (eg. highly disperse silica, silicates); emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

The following are examples of formulations: 1. Products for dilution with water

A Soluble Concentrates (SL)

10 parts by weight of a compound according to the invention are dissolved in water or in a water-soluble solvent. As an alternative, wetters or other auxiliaries are added. The active ingredient dissolves upon dilution with water.

B Dispersible Concentrates (DC)

20 parts by weight of a compound according to the invention are dissolved in cyclohexanone with addition of a dispersant, for example polyvinylpyrrolidone. Dilution with water gives a dispersion.

C Emulsifiable Concentrates (EC)

15 parts by weight of a compound according to the invention are dissolved in xylene with addition of calcium dodecylbenzenesulfonate and castor oil ethoxylate (in each case 5% strength). Dilution with water gives an emulsion.

D Emulsions (EW, EO)

40 parts by weight of a compound according to the invention are dissolved in xylene with addition of calcium dodecylbenzenesulfonate and castor oil ethoxylate (in each case 5% strength). This mixture is introduced into water by means of an emulsifier (ULTRATURRAX) and made into a homogeneous emulsion. Dilution with water gives an emulsion.

E Suspensions (SC, OD)

In an agitated ball mill, 20 parts by weight of a compound according to the invention are comminuted with addition of dispersant, wetters and water or an organic solvent to give a fine active ingredient suspension. Dilution with water gives a stable suspension of the active ingredient.

F Water-dispersible Granules and Water-Soluble Granules (WG, SG)

50 parts by weight of a compound according to the invention are ground finely with addition of dispersants and wetters and made into water-dispersible or water-soluble granules by means of technical appliances (for example extrusion, spray tower, fluidized bed). Dilution with water gives a stable dispersion or solution of the active ingredient.

G Water-dispersible Powders and Water-Soluble Powders (WP, SP)

75 parts by weight of a compound according to the invention are ground in a rotor-stator mill with addition of dispersant, wetters and silica gel. Dilution with water gives a stable dispersion or solution with the active ingredient.

2. Products to be Applied Undiluted

H Dustable Powders (DP)

5 parts by weight of a compound according to the invention are ground finely and mixed intimately with 95% of finely divided kaolin. This gives a dustable product.

I Granules (GR, FG, GG, MG)

0.5 part by weight of a compound according to the invention is ground finely and associated with 95.5% carriers. Current methods are extrusion, spray-drying or the fluidized bed. This gives granules to be applied undiluted.

J ULV Solutions (UL)

10 parts by weight of a compound according to the invention are dissolved in an organic solvent, for example xylene. This gives a product to be applied undiluted.

The active ingredients can be used as such, in the form of their formulations or the use forms prepared therefrom, eg. in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; it is intended to ensure in each case the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

Various types of oils, wetters, adjuvants, herbicides, fungicides, other pesticides, or bactericides may be added to the active ingredients, if appropriate just immediately prior to use (tank mix). These agents can be admixed with the agents according to the invention in a weight ratio of 1:10 to 10:1.

In the use form as fungicides, the compositions according to the invention can also be present together with other active ingredients, for example with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

acylalanines such as benalaxyl, metalaxyl, ofurace, oxadixyl,
amine derivatives such as aldimorph, dodine, dodemorph, fenpropimorph, fenpropidin, guazatine, iminoctadine, spiroxamin, tridemorph
anilinopyrimidines such as pyrimethanil, mepanipyrim or cyrodinyl,
antibiotics such as cycloheximid, griseofulvin, kasugamycin, natamycin, polyoxin or streptomycin,
azoles such as bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole,
dicarboximides such as iprodion, myclozolin, procymidon, vinclozolin,
dithiocarbamates such as ferbam, nabam, maneb, mancozeb, metam, metiram, propineb, polycarbamate, thiram, ziram, zineb,
heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine,
copper fungicides such as Bordeaux mixture, copper acetate, copper oxychloride, basic copper sulfate,
nitrophenyl derivatives such as binapacryl, dinocap, dinobuton, nitrophthalisopropyl
phenylpyrroles such as fenpiclonil or fludioxonil,
sulfur
other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid
strobilurins such as azoxystrobin, dimoxystrobin, fluoxastrobin, kresoxim-methyl, metominostrobin, orysastrobin, picoxystrobin, pyraclostrobin or trifloxystrobin,
sulfenic acid derivatives such as captafol, captan, dichlofluanid, folpet, tolylfluanid
cinnemamides and analogs such as dimethomorph, flumetover or flumorph.

SYNTHESIS EXAMPLES

With due modification of the starting compounds, the protocols shown in the synthesis examples below were used for obtaining further compounds I. The resulting compounds I, together with physical data, are listed in the Table I which follows.

Example 1

Preparation of diethyl(2,3,5-trifluorophenyl)-malonate

Ethyl 2-(2,3,5-trifluorophenyl)-acetate (29 g) was slowly added to a mixture of diethylcarbonate (63 g) and sodium hydride (9.5 g) in toluene (350 ml). After being refluxed for 3 hours, the reaction mixture was cooled, treated with ice-water and washed with water. The organic layer was separated, dried and filtered. The filtrate was concentrated in vacuo to yield 32 g of the title compound.

Example 2

Preparation of 5,7-dihydroxy-6-(2,3,5-trifluorophenyl)-[1,2,4]-triazolo-[1,5-a]pyrimidine A mixture of 3-amino-1,2,4-triazole (14 g), diethyl(2,3,5-trifluorophenyl)-malonate (0.17 mol, obtained from Ex. 1) and tributylamine (50 ml) was heated at 180° C. for six hours. The reaction mixture was cooled to about 70° C. After addition of aqueous sodium hydroxide (21 g/200 ml $H_2O$) the reaction mixture was stirred for 30 minutes. After separation of the organic phase the aqueous phase was extracted with diethyl ether. The aqueous phase was acidified with concentrated hydrochloric acid. The precipitate was collected by filtration and dried to yield 43 g of the title compound.

Example 3

Preparation of 5,7-dichloro-6-(2,3,5-trifluorophenyl)-[1,2,4]-triazolo-[1,5-a]pyrimidine A mixture of 5,7-dihydroxy-6-(2,3,5-trifluorophenyl)-[1,2,4]-triazolo-[1,5-a]pyrimidine (30 g, obtained from Ex. 2) and phosphorous oxychloride (50 ml) is refluxed for 8 h. Phosphorous oxychloride partly distilled off. The residue was poured into a mixture of dichloromethane and water. The organic layer was separated, dried and filtered. The filtrate was concentrated in vacuo to yield 26 g of the title compound of mp. 191° C.

Example 4

Preparation of 5-chloro-6-(2,3,5-trifluorophenyl)-7-isopropylamino-[1,2,4]-triazolo[1,5-a]pyrimidine [I-2]

A mixture of isopropylamine (1.5 mmol), triethylamine (1.5 mmol) and dichloromethane (10 ml) was added to a mixture of 5,7-dichloro-6-(2,3,5-trifluorophenyl)-[1,2,4]-triazolo[1,5-a]pyrimidine (1.5 mmol, obtained from Ex. 3) and dichloromethane (20 ml) under stirring. The reaction mixture was stirred for 16 h. at 20 to 25° C. and washed with 5% hydrochloric acid. The organic layer was separated, dried and filtered. The filtrate was evaporated and the residue was purified by column chromatography to yield 0.42 g of the title compound of mp. 151° C.

Example 5

Preparation of 5-cyano-6-(2-chloro-4-fluorophenyl)-7-(4-methylpiperidin-1-yl)-[1,2,4]-triazolo[1,5-a] pyrimidine A mixture of 5-chloro-6-(2-chloro-4-fluorophenyl)-7-(4-methylpiperidin-1-yl)-[1,2,4]-triazolo-[1,5-a]-pyrimidine (0.1 mol) and tetraethylammonium cyanide (0.25 mol) in 750 ml Dimethylformamide (DMF) was stirred for 16 hours at 20 to 25° C. To this mixture was added water and methyl-tert. butylether (MTBE), the organic phase was separated, washed with water, dried and filtered. The filtrate was evaporated and the residue was purified by column chromatography to yield 5.91 g of the title compound of mp. 247° C.

Example 6

Preparation of 5-methoxy-6-(2-chloro-4-fluorophenyl)-7-(4-methylpiperidin-1-yl)-[1,2,4]-triazolo[1,5-a]pyrimidine To a solution of 5-chloro-6-(2-chloro-4-fluorophenyl)-7-(4-methyl)-piperidin-1-yl)-[1,2,4]-triazolo-[1,5-a]-pyrimidine (65 mmol) in 400 ml dry methanol was added a solution of sodium methanolate (30%, 71.5 mmol) at 20 to 25° C. This mixture was stirred for 16 hours at 20 to 25° C. Methanol was evaporated and the residue was dissolved with dichloromethane. The organic phase was washed with water, dried and filtered. The filtrate was evaporated under reduced pressure and the residue was purified by column chromatography to yield 4.52 g of the title compound of mp. 186° C.

Example 7

Preparation of 5-methyl-6-(2-chloro-4-fluorophenyl)-7-(4-methylpiperidin-1-yl)-[1,2,4]-triazolo[1,5-a]pyrimidine A mixture of 20 ml diethyl malonate and NaH (0.27 g of a 50% dispersion in mineral oil, 5,65 mmol) in 50 ml acetonitrile was stirred at 20 to 25° C. for about 2 hours. To this mixture 5-chloro-6-(2-chloro-4-fluorophenyl)-7-(4-methylpiperidin-1-yl)-[1,2,4]-triazolo-[1,5-a]-pyrimidine (4.71 mmol) was added. The reaction mixture was heated to 60° C. and stirred for about 20 hours. Aqueous ammonium chloride (50 ml) was added and the mixture was acidified with diluted HCl. The reaction mixture was extracted with MTBE. The combined organic phases were dried and concentrated. The residue was purified by column chromatography.

The pure product obtained was diluted in concentrated HCl and heated to 80° C. for about 24 hours. This reaction mixture was cooled and adjusted to pH of 5 by addition of aqueous NaOH, and subsequently extracted with MTBE. The combined organic phases were dried, concentrated and purified by column chromatography to yield 0.78 g of the title compound of mp. 236° C.

TABLE I

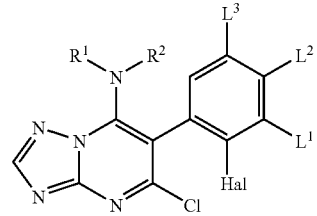

I

| No. | $R^1$ | $R^2$ | Hal | $L^1$ | $L^2$ | $L^3$ | phys. data (m.p. [° C.]) |
|---|---|---|---|---|---|---|---|
| I-1 | $CH_2C(CH_3)=CH_2$ | $CH_2CH_3$ | F | F | H | F | 128 |
| I-2 | $CH(CH_3)_2$ | H | F | F | H | F | 151 |
| I-3 | —$(CH_2)_2CH(CH_3)(CH_2)_2$— | | F | F | H | F | 171 |
| I-4 | cyclopentyl | H | F | F | H | F | 111 |
| I-5 | $CH_2CH_3$ | $CH_2CH_3$ | F | F | H | F | 165 |
| I-6 | $CH_2CH_2CH_3$ | $CH_2CH_2CH_3$ | F | F | H | F | 107 |
| I-7 | $CH(CH_3)_2$ | $CH_3$ | F | F | H | F | 172 |
| I-8 | (±) $CH(CH_3)$—$CH_2CH_3$ | H | F | F | H | F | 99 |
| I-9 | (S) $CH(CH_3)$—$CH_2CH_3$ | H | F | F | H | F | 94 |
| I-10 | (R) $CH(CH_3)$—$CH_2CH_3$ | H | F | F | H | F | 94 |
| I-11 | (±) $CH(CH_3)$—$CH(CH_3)_2$ | H | F | F | H | F | 113/114 |
| I-12 | (S) $CH(CH_3)$—$CH(CH_3)_2$ | H | F | F | H | F | 108/122 |
| I-13 | (R) $CH(CH_3)$—$CH(CH_3)_2$ | H | F | F | H | F | 108/122 |
| I-14 | (±) $CH(CH_3)$—$C(CH_3)_3$ | H | F | F | H | F | 138/129 |
| I-15 | (S) $CH(CH_3)$—$C(CH_3)_3$ | H | F | F | H | F | 129/121 |
| I-16 | (R) $CH(CH_3)$—$C(CH_3)_3$ | H | F | F | H | F | 129/121 |
| I-17 | (±) $CH(CH_3)$—$CF_3$ | H | F | F | H | F | 164 |
| I-18 | (S) $CH(CH_3)$—$CF_3$ | H | F | F | H | F | 147 |
| I-19 | (R) $CH(CH_3)$—$CF_3$ | H | F | F | H | F | 147 |
| I-20 | $CH_2CF_3$ | H | F | F | H | F | 161 |
| I-21 | $CH_2C(CH_3)=CH_2$ | $CH_2CH_3$ | F | H | F | H | 105 |
| I-22 | $CH(CH_3)_2$ | H | F | H | F | H | 159 |
| I-23 | —$(CH_2)_2CH(CH_3)(CH_2)_2$— | | F | H | F | H | 208 |
| I-24 | (±) $CH(CH_3)$—$CH_2CH_3$ | H | F | H | F | H | 86 |
| I-25 | (±) $CH(CH_3)$—$C(CH_3)_3$ | H | F | H | F | H | 160 |
| I-26 | (±) $CH(CH_3)$—$CF_3$ | H | F | H | F | H | 151 |
| I-27 | (S) $CH(CH_3)$—$CF_3$ | H | F | H | F | H | 116 |
| I-28 | $CH_2CF_3$ | H | F | H | F | H | 181 |
| I-29 | $CH(CH_3)_2$ | H | F | H | Br | H | 83 |
| I-30 | —$(CH_2)_2CH(CH_3)(CH_2)_2$— | | F | H | Br | H | 175 |
| I-31 | cyclopentyl | H | F | H | Br | H | 161 |
| I-32 | $CH_2CH_3$ | $CH_2CH_3$ | F | H | Br | H | 142 |
| I-33 | (±) $CH(CH_3)$—$CH_2CH_3$ | H | F | H | Br | H | 81 |
| I-34 | (±) $CH(CH_3)$—$C(CH_3)_3$ | H | F | H | Br | H | 196 |

TABLE I-continued

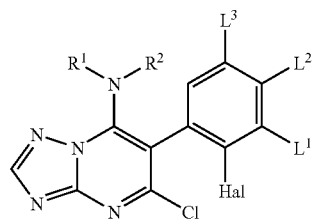

| No. | R¹ | R² | Hal | L¹ | L² | L³ | phys. data (m.p. [° C.]) |
|---|---|---|---|---|---|---|---|
| I-35 | (±) CH(CH₃)—CF₃ | H | F | H | Br | H | 157 |
| I-36 | CH₂CF₃ | H | F | H | Br | H | 108 |
| I-37 | CH₂C(CH₃)=CH₂ | CH₂CH₃ | F | F | H | H | 116 |
| I-38 | CH(CH₃)₂ | H | F | F | H | H | 138 |
| I-39 | —(CH₂)₂CH(CH₃)(CH₂)₂— | | F | F | H | H | 208 |
| I-40 | cyclopentyl | H | F | F | H | H | 65 |
| I-41 | CH₂CH₃ | CH₂CH₃ | F | F | H | H | 135 |
| I-42 | (±) CH(CH₃)—C(CH₃)₃ | H | F | F | H | H | 140 |
| I-43 | CH₂C(CH₃)=CH₂ | CH₂CH₃ | F | H | H | F | 121 |
| I-44 | —(CH₂)₂CH(CH₃)(CH₂)₂— | | F | H | H | F | 181 |
| I-45 | (±) CH(CH₃)—CH₂CH₃ | H | F | H | H | F | 134 |
| I-46 | (±) CH(CH₃)—C(CH₃)₃ | H | F | H | H | F | 184 |
| I-47 | CH₂C(CH₃)=CH₂ | CH₂CH₃ | F | H | F | F | 138 |
| I-48 | CH(CH₃)₂ | H | F | H | F | F | 138 |
| I-49 | —(CH₂)₂CH(CH₃)(CH₂)₂— | | F | H | F | F | 192 |
| I-50 | cyclopentyl | H | F | H | F | F | 165 |
| I-51 | (±) CH(CH₃)—C(CH₃)₃ | H | F | H | F | F | 149 |
| I-52 | (±) CH(CH₃)—CF₃ | H | F | H | F | F | 159 |
| I-53 | CH₂CF₃ | H | F | H | F | F | 178 |
| I-54 | CH(CH₃)₂ | H | F | F | F | H | 139 |
| I-55 | —(CH₂)₂CH(CH₃)(CH₂)₂— | | F | F | F | H | 241 |
| I-56 | CH₂CH₃ | CH₂CH₃ | F | F | F | H | 152 |
| I-57 | (±) CH(CH₃)—CH₂CH₃ | H | F | F | F | H | 123 |
| I-58 | (±) CH(CH₃)—C(CH₃)₃ | H | F | F | F | H | 160 |
| I-59 | (±) CH(CH₃)—CF₃ | H | F | F | F | H | 157 |
| I-60 | CH₂CF₃ | H | F | F | F | H | 174 |
| I-61 | —(CH₂)₂CH(CH₃)(CH₂)₂— | | F | H | NH₂ | H | 249 |
| I-62 | (±) CH(CH₃)—CF₃ | H | F | H | NH₂ | H | 196 |
| I-63 | —(CH₂)₂CH(CH₃)(CH₂)₂— | | F | H | N(CH₃)₂ | H | 143 |
| I-64 | (±) CH(CH₃)—CF₃ | H | F | H | N(CH₃)₂ | H | 147 |
| I-65 | —(CH₂)₂CH(CH₃)(CH₂)₂— | | F | H | NHCOCH₃ | H | 135 |
| I-66 | (±) CH(CH₃)—CF₃ | H | F | H | NHCOCH₃ | H | 147 |
| I-67 | CH₂C(CH₃)=CH₂ | CH₂CH₃ | Br | F | H | F | 139 |
| I-68 | CH(CH₃)₂ | H | Br | F | H | F | 138 |
| I-69 | —(CH₂)₂CH(CH₃)(CH₂)₂— | | Br | F | H | F | 153 |
| I-70 | cyclopentyl | H | Br | F | H | F | 117 |
| I-71 | (±) CH(CH₃)—CH₂CH₃ | H | Br | F | H | F | 121 |
| I-72 | (S) CH(CH₃)—CH₂CH₃ | H | Br | F | H | F | 133 |
| I-73 | (R) CH(CH₃)—CH₂CH₃ | H | Br | F | H | F | 133 |
| I-74 | (±) CH(CH₃)—CH(CH₃)₂ | H | Br | F | H | F | 113 |
| I-75 | (S) CH(CH₃)—CH(CH₃)₂ | H | Br | F | H | F | 125 |
| I-76 | (R) CH(CH₃)—CH(CH₃)₂ | H | Br | F | H | F | 125 |
| I-77 | (±) CH(CH₃)—C(CH₃)₃ | H | Br | F | H | F | 119 |
| I-78 | (S) CH(CH₃)—C(CH₃)₃ | H | Br | F | H | F | 130 |
| I-79 | (R) CH(CH₃)—C(CH₃)₃ | H | Br | F | H | F | 130 |
| I-80 | (±) CH(CH₃)—CF₃ | H | Br | F | H | F | 65 |
| I-81 | (S) CH(CH₃)—CF₃ | H | Br | F | H | F | 78 |
| I-82 | (R) CH(CH₃)—CF₃ | H | Br | F | H | F | 78 |
| I-83 | (S) CH(CH₃)—CH₂CH₃ | H | F | H | F | H | 79 |
| I-84 | (R) CH(CH₃)—CH₂CH₃ | H | F | H | F | H | 79 |
| I-85 | (S) CH(CH₃)—CH(CH₃)₂ | H | F | H | F | H | 133 |
| I-86 | (R) CH(CH₃)—CH(CH₃)₂ | H | F | H | F | H | 133 |
| I-87 | (S) CH(CH₃)—C(CH₃)₃ | H | F | H | F | H | 161 |
| I-88 | (R) CH(CH₃)—C(CH₃)₃ | H | F | H | F | H | 161 |
| I-89 | (R) CH(CH₃)—CF₃ | H | F | H | F | H | 116 |
| I-90 | CH₂C(CH₃)=CH₂ | CH₂CH₃ | F | H | Cl | H | 123 |
| I-91 | (±) CH(CH₃)—CH₂CH₃ | H | F | H | Cl | H | 110 |
| I-92 | (S) CH(CH₃)—CH₂CH₃ | H | F | H | Cl | H | 99 |
| I-93 | (R) CH(CH₃)—CH₂CH₃ | H | F | H | Cl | H | 99 |
| I-94 | (±) CH(CH₃)—CH(CH₃)₂ | H | F | H | Cl | H | 141 |
| I-95 | (S) CH(CH₃)—CH(CH₃)₂ | H | F | H | Cl | H | 131 |
| I-96 | (R) CH(CH₃)—CH(CH₃)₂ | H | F | H | Cl | H | 131 |
| I-97 | (±) CH(CH₃)—C(CH₃)₃ | H | F | H | Cl | H | 191 |
| I-98 | (S) CH(CH₃)—C(CH₃)₃ | H | F | H | Cl | H | 186 |

TABLE I-continued

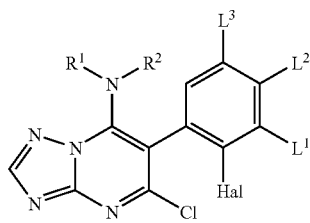

| No. | $R^1$ | $R^2$ | Hal | $L^1$ | $L^2$ | $L^3$ | phys. data (m.p. [° C.]) |
|---|---|---|---|---|---|---|---|
| I-99 | (R) CH(CH$_3$)—C(CH$_3$)$_3$ | H | F | H | Cl | H | 185 |
| I-100 | (±) CH(CH$_3$)—CF$_3$ | H | F | H | Cl | H | 162 |
| I-101 | (S) CH(CH$_3$)—CF$_3$ | H | F | H | Cl | H | 162 |
| I-102 | (R) CH(CH$_3$)—CF$_3$ | H | F | H | Cl | H | 162 |
| I-103 | CH$_2$CF$_3$ | H | F | H | Cl | H | 146 |
| I-104 | C(CH$_3$)CH(CH$_3$)$_2$ | H | F | H | F | H | 130 |
| I-105 | CH$_2$C(CH$_3$)=CH$_2$ | CH$_2$CH$_3$ | F | H | CF$_3$ | H | 140 |
| I-106 | —(CH$_2$)$_2$CH(CH$_3$)(CH$_2$)$_2$— | | F | H | CF$_3$ | H | 177 |
| I-107 | (±) CH(CH$_3$)—CH$_2$CH$_3$ | H | F | H | CF$_3$ | H | 137 |
| I-108 | (S) CH(CH$_3$)—CH$_2$CH$_3$ | H | F | H | CF$_3$ | H | 128 |
| I-109 | (R) CH(CH$_3$)—CH$_2$CH$_3$ | H | F | H | CF$_3$ | H | 128 |
| I-110 | (±) CH(CH$_3$)—CH(CH$_3$)$_2$ | H | F | H | CF$_3$ | H | 150 |
| I-111 | (S) CH(CH$_3$)—CH(CH$_3$)$_2$ | H | F | H | CF$_3$ | H | 143 |
| I-112 | (R) CH(CH$_3$)—CH(CH$_3$)$_2$ | H | F | H | CF$_3$ | H | 143 |
| I-113 | (±) CH(CH$_3$)—C(CH$_3$)$_3$ | H | F | H | CF$_3$ | H | 193 |
| I-114 | (S) CH(CH$_3$)—C(CH$_3$)$_3$ | H | F | H | CF$_3$ | H | 195 |
| I-115 | (R) CH(CH$_3$)—C(CH$_3$)$_3$ | H | F | H | CF$_3$ | H | 194 |
| I-116 | (±) CH(CH$_3$)—CF$_3$ | H | F | H | CF$_3$ | H | 167 |
| I-117 | (S) CH(CH$_3$)—CF$_3$ | H | F | H | CF$_3$ | H | 135 |
| I-118 | (R) CH(CH$_3$)—CF$_3$ | H | F | H | CF$_3$ | H | 135 |
| I-119 | CH$_2$CF$_3$ | H | F | H | CF$_3$ | H | 143 |
| I-120 | CH$_2$C(CH$_3$)=CH$_2$ | CH$_2$CH$_3$ | F | H | H | CH$_3$ | 121 |
| I-121 | —(CH$_2$)$_2$CH(CH$_3$)(CH$_2$)$_2$— | | F | H | H | CH$_3$ | 141 |
| I-122 | (±) CH(CH$_3$)—CH$_2$CH$_3$ | H | F | H | H | CH$_3$ | 134 |
| I-123 | (S) CH(CH$_3$)—CH$_2$CH$_3$ | H | F | H | H | CH$_3$ | 131 |
| I-124 | (R) CH(CH$_3$)—CH$_2$CH$_3$ | H | F | H | H | CH$_3$ | 131 |
| I-125 | (±) CH(CH$_3$)—CH(CH$_3$)$_2$ | H | F | H | H | CH$_3$ | 158 |
| I-126 | (S) CH(CH$_3$)—CH(CH$_3$)$_2$ | H | F | H | H | CH$_3$ | 159 |
| I-127 | (R) CH(CH$_3$)—CH(CH$_3$)$_2$ | H | F | H | H | CH$_3$ | 159 |
| I-128 | (±) CH(CH$_3$)—C(CH$_3$)$_3$ | H | F | H | H | CH$_3$ | 181 |
| I-129 | (S) CH(CH$_3$)—C(CH$_3$)$_3$ | H | F | H | H | CH$_3$ | 171 |
| I-130 | (R) CH(CH$_3$)—C(CH$_3$)$_3$ | H | F | H | H | CH$_3$ | 171 |
| I-131 | (±) CH(CH$_3$)—CF$_3$ | H | F | H | H | CH$_3$ | 170 |
| I-132 | (S) CH(CH$_3$)—CF$_3$ | H | F | H | H | CH$_3$ | 140 |
| I-133 | (R) CH(CH$_3$)—CF$_3$ | H | F | H | H | CH$_3$ | 140 |
| I-134 | CH$_2$CF$_3$ | H | F | H | H | CH$_3$ | 185 |
| I-135 | CH$_2$C(CH$_3$)=CH$_2$ | CH$_2$CH$_3$ | Cl | H | F | H | 128 |
| I-136 | —(CH$_2$)$_2$CH(CH$_3$)(CH$_2$)$_2$— | | Cl | H | F | H | 124 |
| I-137 | (±) CH(CH$_3$)—CH$_2$CH$_3$ | H | Cl | H | F | H | 155 |
| I-138 | (S) CH(CH$_3$)—CH$_2$CH$_3$ | H | Cl | H | F | H | 130 |
| I-139 | (R) CH(CH$_3$)—CH$_2$CH$_3$ | H | Cl | H | F | H | 131 |
| I-140 | (±) CH(CH$_3$)—CH(CH$_3$)$_2$ | H | Cl | H | F | H | 121 |
| I-141 | (S) CH(CH$_3$)—CH(CH$_3$)$_2$ | H | Cl | H | F | H | 108 |
| I-142 | (R) CH(CH$_3$)—CH(CH$_3$)$_2$ | H | Cl | H | F | H | 109 |
| I-143 | (±) CH(CH$_3$)—C(CH$_3$)$_3$ | H | Cl | H | F | H | 156 |
| I-144 | (S) CH(CH$_3$)—C(CH$_3$)$_3$ | H | Cl | H | F | H | 153 |
| I-145 | (R) CH(CH$_3$)—C(CH$_3$)$_3$ | H | Cl | H | F | H | 153 |
| I-146 | (±) CH(CH$_3$)—CF$_3$ | H | Cl | H | F | H | 194 |
| I-147 | (S) CH(CH$_3$)—CF$_3$ | H | Cl | H | F | H | 155 |
| I-148 | (R) CH(CH$_3$)—CF$_3$ | H | Cl | H | F | H | 155 |
| I-149 | CH$_2$CF$_3$ | H | Cl | H | F | H | 176 |
| I-150 | —(CH$_2$)$_2$CH(CH$_3$)(CH$_2$)$_2$— | | F | H | Cl | H | 187 |
| I-151 | (±) CH(CH$_3$)—CH$_2$CH$_3$ | H | F | F | H | H | 133 |
| I-152 | (S) CH(CH$_3$)—CH$_2$CH$_3$ | H | F | F | H | H | 137 |
| I-153 | (R) CH(CH$_3$)—CH$_2$CH$_3$ | H | F | F | H | H | 137 |
| I-154 | (±) CH(CH$_3$)—CH(CH$_3$)$_2$ | H | F | F | H | H | 135 |
| I-155 | (S) CH(CH$_3$)—CH(CH$_3$)$_2$ | H | F | F | H | H | 124 |
| I-156 | (R) CH(CH$_3$)—CH(CH$_3$)$_2$ | H | F | F | H | H | 124 |
| I-157 | (S) CH(CH$_3$)—C(CH$_3$)$_3$ | H | F | F | H | H | 142 |
| I-158 | (R) CH(CH$_3$)—C(CH$_3$)$_3$ | H | F | F | H | H | 142 |
| I-159 | (±) CH(CH$_3$)—CF$_3$ | H | F | F | H | H | 187 |

TABLE I-continued

I $$\text{Structure: } R^1R^2N\text{- substituted triazolopyrimidine with phenyl group bearing } L^1, L^2, L^3, \text{Hal and Cl}$$

| No. | R¹ | R² | Hal | L¹ | L² | L³ | phys. data (m.p. [° C.]) |
|---|---|---|---|---|---|---|---|
| I-160 | (S) CH(CH₃)—CF₃ | H | F | F | H | H | 149 |
| I-161 | (R) CH(CH₃)—CF₃ | H | F | F | H | H | 149 |
| I-162 | CH₂CF₃ | H | F | F | H | H | 186 |
| I-163 | (S) CH(CH₃)—CH₂CH₃ | H | F | H | H | F | 131 |
| I-164 | (R) CH(CH₃)—CH₂CH₃ | H | F | H | H | F | 131 |
| I-165 | (±) CH(CH₃)—CH(CH₃)₂ | H | F | H | H | F | 159 |
| I-166 | (S) CH(CH₃)—CH(CH₃)₂ | H | F | H | H | F | 162 |
| I-167 | (R) CH(CH₃)—CH(CH₃)₂ | H | F | H | H | F | 162 |
| I-168 | (S) CH(CH₃)—C(CH₃)₃ | H | F | H | H | F | 180 |
| I-169 | (R) CH(CH₃)—C(CH₃)₃ | H | F | H | H | F | 180 |
| I-170 | (±) CH(CH₃)—CF₃ | H | F | H | H | F | 63 |
| I-171 | (S) CH(CH₃)—CF₃ | H | F | H | H | F | 59 |
| I-172 | (R) CH(CH₃)—CF₃ | H | F | H | H | F | 59 |
| I-173 | CH₂C(CH₃)=CH₂ | CH₂CH₃ | F | H | NO₂ | H | 170 |
| I-174 | CH(CH₃)₂ | H | F | H | NO₂ | H | 169 |
| I-175 | —(CH₂)₂CH(CH₃)(CH₂)₂— | | F | H | NO₂ | H | 231 |
| I-176 | cyclopentyl | H | F | H | NO₂ | H | 201 |
| I-177 | (±) CH(CH₃)—C(CH₃)₃ | H | F | H | NO₂ | H | 165 |
| I-178 | (±) CH(CH₃)—CF₃ | H | F | H | NO₂ | H | 241 |
| I-179 | CH₂CF₃ | H | F | H | NO₂ | H | 237 |
| I-180 | CH₂C(CH₃)=CH₂ | CH₂CH₃ | Cl | H | NO₂ | H | 166 |
| I-181 | —(CH₂)₂CH(CH₃)(CH₂)₂— | | Cl | H | NO₂ | H | 204 |

In some cases of chiral groups R¹ and due to the hindered rotation of the phenyl group two diastereomers exist which may differ in their physical properties.

Examples for the action against harmful fungi

The fungicidal action of the compounds of formula I was demonstrated by the following experiments:

The active ingredients, separately or jointly, were used to prepare a stock solution comprising 0.25% by weight of active ingredient in acetone or DMSO. 1% by weight of the emulsifier UNIPEROL® EL (emulsifying and dispersing wetter based on ethoxylated alkylphenols) was added to this solution and the mixture was diluted with water to give the desired concentration.

Use Example 1

Fungicidal Control of Early Blight on Tomatoes (*Alternaria solani*)

Leaves of pot grown tomato seedlings of the "Große Fleischtomate St. Pierre" variety were sprayed with an aqueous suspension containing the active compound in the concentration mentioned below. The next day the leaves were infected with a zoospore suspension of *Alternaria solani* (0.17×10⁶ spores per ml of a 2% strength biomalt solution). The plants were then placed in a water vapour-saturated chamber at 20 to 22° C. After 5 days the disease had spread to such a great extent on the untreated plants that the fungicidal activity of the substances could be assessed.

In this test, the plants which had been treated with 250 ppm of compounds I-2, I-4, I-8, I-17, I-20, I-21, I-25, I-28, I-90, I-91, I-94, I-97, and I-101, resp., showed an infection of not more than 7%, whereas the untrated plants were infected to 90%.

Use Example 2

Control of Gray Mould (*Botrytis cinerea*) on Paprika Leaves

Paprika seedlings were sprayed to run-off at the four- to five leave stage with an aqueous suspension containing the concentration of active ingredient mentioned below. The next day the plants were inoculated with a spore suspension of *Botrytis cinerea* containing 1.7×10⁶ spores per ml in 2 wt. % aqueous biomalt solution. The infected plants were then incubated in chambers with high humidity for five days at 22-24° C. The extent of fungus spread was assessed as %-attack of the whole leaf surface.

In this test, the plants which had been treated with 250 ppm of compounds I-2, I-4, I-5, I-8, I-17, and I-20, resp., showed an infection of not more than 5%, whereas the the unteated plants were infected to 85%.

Use Example 3

Fungicidal Control of Grape Downy Mildew (*Plasmopara viticola*)

Leaves of potted vines of the "Müller Thurgau" variety were sprayed with aqueous liquors made from a stock solution containing the concentration of active ingredient mentioned below. The next day they were inoculated with an aqueous spore suspension of *Plasmopara viticola* by spraying it at the lower leaf-side. Then the trial plants were transferred for 48 h to a humid chamber with about 24° C. and a relative humidity close to 100%. For a period of 5 days, cultivation followed in a greenhouse at 20 to 30° C. To stimulate the outbreak of the disease symptoms, the plants were transferred to a humid chamber again for 16 hours. Then the extent of fungal attack on the lower leaf surface was visually assessed as % diseased leaf area.

In this test, the plants which had been treated with 250 ppm of compounds I-2, I-4, I-8, I-17, and 1-20, resp., showed an infection of not more than 15%, whereas the unteated plants were infected to 95%.

Use Example 4

Action on *Pyricularia oryzae* (Protective Action)

Leaves of pot grown rice seedlings of the "Tai-Nong 67" variety were sprayed to runoff with an aqueous suspension, containing the concentration of active ingredient mentioned below. The next day the plants were inoculated with an aqueous spore suspension of *Pyricularia oryzae*. The plants were then placed for 6 days in a humid chamber at 22 to 24° C. and a relative humidity of 95 to 99%. The extent of fungus spread was assessed as %-attack of the whole leaf surface.

In this test, the plants which had been treated with 250 ppm of compounds I-2, I-4, I-5, and I-20, resp., showed an infection of not more than 15%, whereas the unteated plants were infected to 80%.

Use Example 5

Control of Net Blotch on Barley Caused by *Pyrenophora teres*

Leaves of pot grown barley seedlings of the variety "Igri" were sprayed to run-off with an aqueous suspension, containing the concentration of active ingredient mentioned below. The next day the treated plants were inoculated with an aqueous spore suspension of *Pyrenophora* [syn. *Drechslera*] *teres*. Then the trial plants were immediately transferred to a humid chamber in the greenhouse. After 6 days of cultivation at 20-24° C. and a relative humidity close to 100%, the extent of fungal attack on the leaves was visually assessed as % diseased leaf area.

In this test, which had been treated with 250 ppm of compounds I-21, I-25, I-28, I-43, I-45, I-91, I-94, and I-97, resp., showed an infection of not more than 10%, whereas the untreated plants were infected to 90%.

The invention claimed is:

1. A compound of formula I

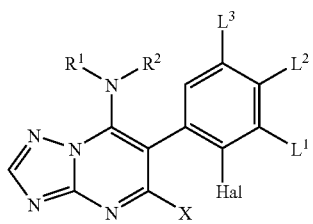

I in which
Hal is halogen;
$L^1, L^3$ independently denote hydrogen, halogen, or $C_1$-$C_4$-alkyl;
$L^2$ is hydrogen, halogen, $C_1$-$C_4$-haloalkyl, or $NH_2$, $NHR^b$, or $N(R^b)_2$,
  $R^b$ is $C_1$-$C_8$-alkyl, or C(=O)-A, in which A is $C_1$-$C_8$-alkyl;
wherein at least one from $L^1$, $L^2$, and $L^3$ is not hydrogen;
X is halogen, $C_1$-$C_6$-alkyl, or $C_1$-$C_6$-alkoxy;
$R^1$ and $R^2$ together with the interjacent nitrogen atom represent a saturated or partially unsaturated 5- or 6-membered heterocycle, containing one nitrogen atom or one nitrogen atom and one sulfur atom, which ring may be substituted by one to three $R^a$ radicals;
$R^a$ is $C_1$-$C_6$ alkyl.

2. The compound of formula I according to claim 1, in which
$R^1$ and $R^2$ together with the interjacent nitrogen atom represent a saturated or partially unsaturated 5- or 6-membered heterocycle, containing one nitrogen atom or one nitrogen atom and one sulfur atom, being optionally substituted with one or two $C_1$-$C_4$-alkyl groups.

3. The compound of formula I according to claim 1 in which $R^1$ and $R^2$ together with the interjacent nitrogen atom represent a saturated or partially unsaturated 5- or 6-membered heterocycle, containing one nitrogen atom or one nitrogen atom and one sulfur atom, being optionally substituted with one or two methyl groups.

4. The compound of formula I according to claim 1 in which X is halogen.

5. The compound of formula I according to claim 1 in which the 6-(2-halogenphenyl) group represents one of the following moieties:

2,3,5-trifluorophenyl; 2-F,4-$CF_3$-phenyl; 2-F,5-$CH_3$-phenyl; 2-Cl, 4-F-phenyl; 2-F,4-Cl-phenyl; 2-F,4-Br-phenyl; 2-Cl,4-Br-phenyl; 2,3-difluorophenyl; 2,4-difluorophenyl; 2,4,5-trifluorophenyl; 2,3,4-trifluorophenyl; 2-F,4-NHC(O)$CH_3$-phenyl; and 2-Br,3,5-difluorophenyl.

6. A process for the preparation of the compound of formula I as defined in claim 4 which comprises reacting 5-amino-1,2,4-triazole

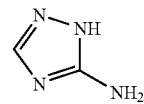

with 2-phenyl-substituted malonic acid ester of formula II,

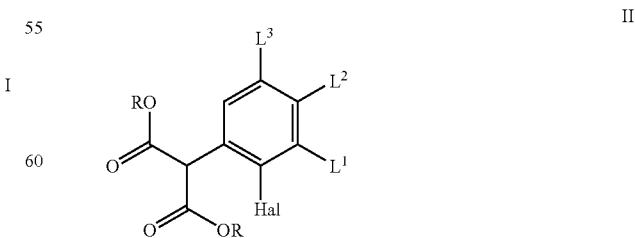

II wherein Hal, $L^1$, $L^2$, and $L^3$ are as defined in formula I, and R denotes $C_1$-$C_6$-alkyl, under alkaline conditions, to yield compounds of formula III,

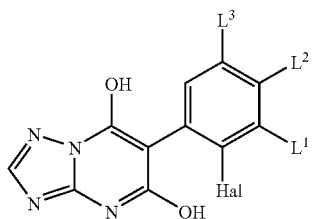

III which are subsequently treated with a halogenating agent to give 5,7-dihalogen-6-phenyl-triazolopyrimidines of formula IV

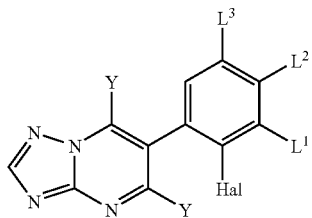

IV in which Y is halogen, and which is reacted with an amine of formula V

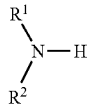

V in which $R^1$ and $R^2$ together with the interjacent nitrogen atom represent a saturated or partially unsaturated 5- or 6-membered heterocycle, containing one nitrogen atom or one nitrogen atom and one sulfur atom, which ring may be substituted by one to three $R^a$ radicals; $R^a$ is $C_1$-$C_6$ alkyl to produce compounds of formula I, as defined in claim 4.

7. A process for the preparation of the compound of formula I according to claim 1 wherein X is $C_1$-$C_{10}$-alkoxy, which comprises reacting 5-halogen-triazolopyrimidine of formula I',

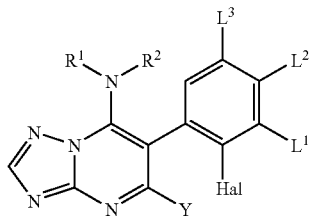

I' wherein Y is halogen, with compounds of formula VI,

M-X'  VI which is an alkoxylate, wherein M is ammonium-, tetraalkylammonium-, alkalimetal- or alkaline earth metal cation, to produce compounds of formula I.

8. A composition suitable for controlling phytopathogenic fungi, comprising a solid or liquid carrier and the compound of the formula I as claimed in claim 1.

9. A method for controlling phytopathogenic fungi, which comprises treating the fungi or the materials, plants, the soil or the seed to be protected against fungal attack with an effective amount of the compound of the formula I as claimed in claim 1.

* * * * *